United States Patent [19]

Audiau et al.

[11] Patent Number: 4,478,841

[45] Date of Patent: Oct. 23, 1984

[54] 3-[2-(TETRA- AND HEXA-HYDRO-4-PYRIDYL)-ETHYL]-INDOLES AND THEIR USE AS MEDICAMENTS

[75] Inventors: Francois Audiau, Charenton; Gérard R. Le Fur, Plessis Robinson, both of France

[73] Assignee: Pharmuka Laboratoires, Gennevilliers, France

[21] Appl. No.: 374,364

[22] Filed: May 3, 1982

[30] Foreign Application Priority Data

May 22, 1981 [FR] France ................... 81 10218

[51] Int. Cl.³ .................. A61K 31/44; A61K 31/445
[52] U.S. Cl. .................. 424/263; 424/267; 546/201; 546/273
[58] Field of Search ............... 546/201, 273; 424/263, 424/267

[56] References Cited

U.S. PATENT DOCUMENTS 4,064,255  12/1977  Champseix et al. ............... 424/267

FOREIGN PATENT DOCUMENTS 1071198  8/1954  France ..................... 546/201
2334358  12/1975  France ..................... 424/267
 925429  5/1963  United Kingdom ........... 546/201

OTHER PUBLICATIONS

Gray et al., Journal of Organic Chemistry, vol. 26, No. 7, pp. 3368-3372, (Sept. 1961).

Primary Examiner—Alan L. Rotman
Attorney, Agent, or Firm—Beveridge, DeGrandi & Kline

[57] ABSTRACT

Compounds of general formula:

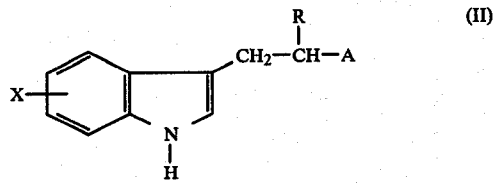

wherein X represents a hydrogen or halogen atom, R represents a hydrogen atom or an alkyl group having 1 to 3 carbon atoms and A represents the 1,2,5,6-tetrahydro-4-pyridyl or the 1,2,3,4,5,6-hexahydro-4-pyridyl radical, with the proviso that when A is the 1,2,3,4,5,6-hexahydro-4-pyridyl radical, R is alkyl having 1 to 3 carbon atoms, are disclosed together with methods for their preparation and their use in the treatment of migraines, as antithrombosis agents or as rapid acting thymoanaleptic medicaments.

4 Claims, No Drawings

3-[2-(TETRA- AND HEXA-HYDRO-4-PYRIDYL)-ETHYL]-INDOLES AND THEIR USE AS MEDICAMENTS

The present invention relates to new indole derivatives and their use as medicaments.

French Pat. No. 75,38051 (U.S. Pat. No. 2,334,358) filed on Dec. 12, 1975, which corresponds to U.S. Pat. No. 4,064,255, describes indole derivatives which are active as specific inhibitors of serotonin uptake by neurons and which may thus be used as psychotropic medicaments, especially as anti-depressants. As such, special reference may be made to 3-[2-(4-piperidyl)-ethyl]-indole of the formula

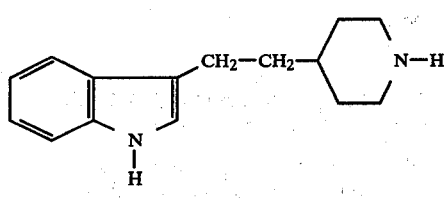

or indalpine, G. Le Fur and coll. Life Sciences, 23, 1959 (1978).

With respect to new products, the object of the present invention is compounds of the general formula:

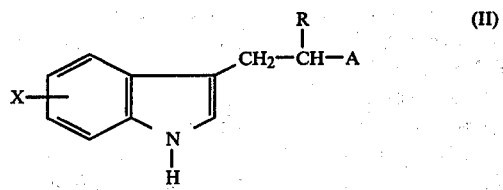

wherein R represents a hydrogen atom or an alkyl group having 1 to 3 carbon atoms, X represents a hydrogen or halogen atom and A ressesents the 1,2,5,6-tetrahydro-4-pyridyl radical, or R represents an alkyl group having 1 to 3 carbon atoms, X represents a hydrogen or halogen atom and A represents the 1,2,3,4,5,6-hexahydro-4-pyridyl radical. Thus, R represents a hydrogen atom or an alkyl group having 1 to 3 carbon atoms, X represents a hydrogen or halogen atom and A represents the 1,2,5,6-tetrahydro-4-pyridyl or 1,2,3,4,5,6-hexahydro-4-pyridyl radical, with the proviso that when A is the 1,2,3,4,5,6-hexahydro-4-pyridyl radical, R is alkyl having 1 to 3 carbon atoms.

The 1,2,3,4,5,6-hexahydro-4-pyridyl radical is also understood in conventional terms as the 4-piperidyl radical.

It has been found according to the present invention that the compounds of formula (II) as defined above, possess not only the ability like indalpine of inhibiting serotonin uptake but also the property of inducing the release of serotonin, which is contained either in the neurons or in the blood platelets.

This dual function reveals itself in a more intense and more rapid action on depression owing to the neuron release of serotonin in the synaptic left, together with inhibition of uptake. The release of serotonin from the platelets into the blood plasma leads to an improvement in migraine conditions; in addition, depletion of the serotonin in the platelets prevents arterial thrombi from forming.

The compounds according to the invention may be prepared by reduction of 3-[2-(4-pyridyl)-ethyl]-indoles corresponding to the general formula:

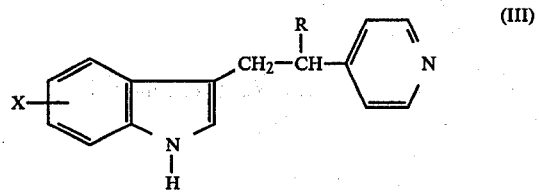

This formula does not include 3-[2-(4-pyridyl)-ethyl]-indole, a known compound used in the preparation of indalpine. The compounds of formula (III) which are used in the preparation of new tetra- and hexahydro derivatives according to the invention are in themselves, new intermediary products. Their reduction may be carried out according to the process described by S. Wawzonek and coll., J. Am. Chem. Soc. vol 74, page 28, 1952.

An advantageous method consists in carrying out reduction with sodium, in an alcohol having 1 to 5 carbon atoms, such as n-butanol, at a temperature of between 80° and 120° C. Under such conditions a mixture of totally saturated products (formula IV) and partially saturated products (formula V) is obtained:

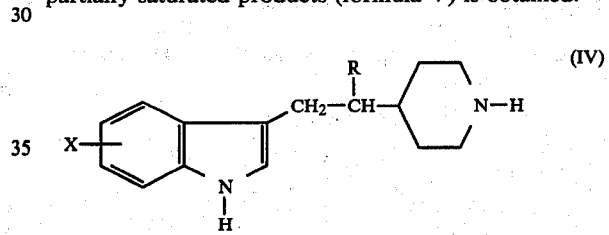

hexahydro pyridyl or piperidyl derivative,

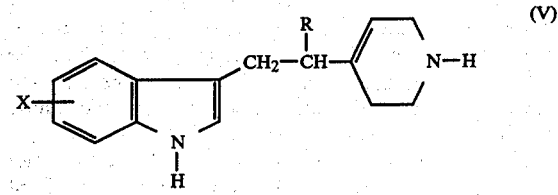

1,2,5,6-tetrahydro derivative.

Separation of the reaction products may be carried out by chromatography and crystallization of the products in the form of a base or a salt.

The products of formula (IV) wherein X represents a hydrogen atom may also be prepared by catalytic hydrogenation of the corresponding compounds of formula (III) or their salts. This hydrogenation is carried out in an inert solvent, at a temperature between 20° and 100° C. and at a pressure of 1 to 50 bars. As examples of solvent, alcohols such as methanol or ethanol, or acids such as acetic acid may be used. Nickel, palladium, rhodium, ruthenium or platinum may be used as the hydrogenation catalyst.

The starting products of formula (III) may be prepared by the reaction of an indole derivative of the formula:

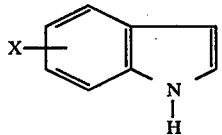

with a pyridine derivative of the formula:

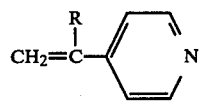

wherein X and R have the same significance as in formula (III). It is advantageous to work in acetic acid at a temperature between 100° and 120° C.

The reaction mixtures obtained according to the various procedures described above are treated according to methods which are conventional, i.e., physical (evaporation, extraction by using a solvent, distillation, crystallization, chromtography, etc.) or chemical (salt formation and regeneration of the base, etc.) so as to isolate the compounds of formula (II) in the pure state.

The compounds of formula (II) in the form of the free base may, if desired, be transformed into addition salts with a pharamceutically acceptable mineral or organic acid, e.g., hydrochloric acid, sulfuric acid, maleic acid or citric acid, by the action of said acid in a suitable solvent, e.g., ethanol, acetone or ethyl acetate.

The following examples illustrate the invention without limiting it.

EXAMPLE 1

3-[2-(1,2,5,6-TETRAHYDRO-4-PYRIDYL)-ETHYL]-INDOLE

A solution of 10.3 g of 3-[2-(4-pyridyl)-ethyl]-indole (prepared according to U.S. Pat. No. 3,300,506) in 400 ml n-butanol was heated, under nitrogen, at a temperature of approximately 90° C. Thereafter, 8 g of sodium were added portionwise while agitating magnetically and the temperature was raised to and maintained at about 110° C. until the sodium disappeared. Once the ambient temperature had been restored, the solution was poured into 400 ml water, the organic phase washed with water until it became neutral and then was dried over sodium sulfate and evaporated under vacuum. The evaporation residue was mixed with 25 ml absolute ethanol and purified by means of chromatography over silica gel, (eluant: ethanol-diethylamine=40-1). Following two processes of crystallization in methanol, 2.6 g of 3-[2-(1,2,5,6-tetrahydro-4-pyridyl)-ethyl]-indole were obtained, which melted at 155° C.

EXAMPLE 2

3-[2-(1,2,5,6-TETRAHYDRO-4-PYRIDYL)-2-METHYL-ETHYL]-INDOLE

The same procedure was adopted as in Example 1, using 11.2 g of 3-[2-(4-pyridyl)-2-methyl-ethyl]-indole; following purification by chromatography over silica gel (eluant: ethanol-diethylamine; 40-1) and crystallization in absolute ethanol, 3.8 g of 3-[2-(1,2,5,6-tetrahydro-4-pyridyl)-2-methyl-ethyl]-indole were obtained, which melted at 125° C.

The starting product was prepared in the following way: the following were brought to reflux for 24 hours: 100 g indole, 450 ml acetic acid and 21.3 g of 4-α-methyl-vinyl-pyridine (prepared according to Clemo and Hoggarth, J. C. S. 1941, 41-7).

The mixture was then poured into 1 liter of iced water, alkalinized with sodium hydroxide, extracted 3 times with 500 ml ethyl acetate each time and the organic phase was washed in water. The organic phase was extracted three times with normal hydrochloric acid. The aqueous acid solution was washed with ethyl acetate, alkalinized with ammonia and the oil was extracted 2 times with 500 ml each time of ethyl acetate. The solvent was evaporated at reduced pressure and the residue purified by means of chromatography over silica gel (eluant: ethyl acetate). Following crystallization in a mixture of toluene and petroleum ether (1-1) 11.2 g of 3-[2-(4-pyridyl)-2-methyl-ethyl]-indole were obtained which melted at 115° C.

EXAMPLE 3

3-[2-(1,2,5,6-TETRAHYDRO-4-PYRIDYL)-ETHYL]-5-FLUORO-INDOLE

The procedure was according to Example 1 using 12 g 3-[2-(4-pyridyl)-ethyl]-5-fluoro-indole. Following purification by chromatography over silica gel (eluant: toluene-ethanol-diethylamine: 10-10-1) 3.5 g of 3-[2-(1,2,5,6-tetrahydro-4-pyridyl)-ethyl]-5-fluoro-indole were obtained, whose fumaric acid salt melted at 208°–210° C.

The starting product was prepared according to the same procedure as that described in the last paragraph of Example 2. 9.5 g of 5-fluoro-indole (U.S. Pat. No. 879,619) and 11 g 4-vinyl-pyridine were refluxed for 6 hours in 50 ml acetic acid. The mixture was then poured onto 300 g of crushed ice and alkalinized with a 20% potassium carbonate solution. A precipitate formed which was squeezed and washed in water several times. After drying under vacuum, 12 g of 3-[2-(4-pyridyl)-ethyl]-5-fluoro-indole were obtained which melted at 128° C.

EXAMPLE 4

3-[2-(4-PIPERIDYL)-2-METHYL-ETHYL]-INDOLE

The same procedure as in Example 2 was adopted. Following elution of 3-[2-(1,2,5,6-tetrahydro-4-pyridyl)-2-methyl-ethyl]-indole, chromatography was carried out with an ethanol-diethylamine mixture (9-1). After crystallization in absolute ethanol, 2.3 g of 3-[2-(4-piperidyl)-2-methyl-ethyl]-indole were obtained, which melted at 150° C.

EXAMPLE 5

0.8 g of 3-[2-(4-pyridyl)-2-methyl-ethyl]-indole were hydrogenated at atmospheric pressure for a period of 15 hours at 60° C. in 20 ml acetic acid in the presence of 0.4 g platinum oxide. The catalyst was eliminated by filtration and the filtrate evaporated. The residue was purified by chromatography over silica (eluant: ethanol-diethylamine: 9-1). 0.25 g 3-[2-(4-piperidyl)-2-methyl-ethyl]-indole were obtained which were converted into the hydrochloride in ethanol. 0.15 g 3-[2-(4-piperidyl)-2-methyl-ethyl]-indole hydrochloride were obtained, which melted at 210° C.

PHARMACOLOGICAL PROPERTIES

It is known that serotonin uptake by the blood platelets is a good model of the uptake of this amine by the neurons (cf. J. Tuomisto, J. Pharm., Pharmac., 26, 92 (1974). When applied to the study of medicaments, a method involving the use of blood platelets is of great interest because it allows the use of human cells so that its anticipation character is good.

The capacity of products to inhibit serotonin uptake or to induce serotonin release, was shown on human blood platelets, according to J. L. David and Coll. "Platelets Function and Thrombosis, a Review of Methods" p. 335 (Plenum Press, London, 1972).

1. Inhibition of Serotonin uptake

The results are expressed by a 50% inhibiting dose or $I_{50}$ which represents the product dose, in micromoles per liter, which reduces the rate of serotonin uptake by 50%.

2. Serotonin Release

The action of the products on serotonin release is tested at a concentration of $5 \times 10^{-5}$ moles per liter. The results obtained are expressed as a percentage of increased serotonin release in relation to the results obtained with controls.

The results obtained with the compounds according to the invention are compiled in the table below. This table shows, as a comparison, the results obtained with two reference products (imipramine and p-chloroamphetamine) and with indalpine.

TABLE

| Product | Inhibition of serotonin uptake $I_{50}$ (micromoles per liter) | Percent of increased serotonin release (product concentration: $5 \times 10^{-5}$ moles per liter) |
| --- | --- | --- |
| Example 1 | 0.055 | 85 |
| Example 2 | 0.04 | 68 |
| Example 4 | 0.01 | 76 |
| Indalpine | 0.035 | 22 |
| Imipramine | 0.4 | 13 |
| p-chloroamphetamine | 12 | 51 |

It can be seen from the table that the products of the invention are not only powerful inhibitors of serotonin uptake (activity equivalent to that of indalpine) but are, moreover, powerful agents of serotonin release, which are even more active than p-chloro-amphetamine.

The interesting feature of these compounds lies in the fact that, like parachloroamphetamine, they induce serotonin release without presenting any of the pharmacological properties which characterize amphetamines (anorexia, hypermotility).

TOXICOLOGICAL PROPERTIES

The acute toxicity of the products has been established in the male $CD_1$ (Charles RIVER) mice following oral administration. The $LD_{50}$ calculated following 3 days of observation by the cumulative method of J. J. Reed and Coll. (Am. J. Hyg. 27, 493-1938) is 600 mg/kg for compounds of Examples 1 and 2 and about 400 mg/kg for the compound of Example 4.

The compounds according to the invention are atoxic at 100 mg/kg and act as relatively non-toxic substances when administered to mice.

THERAPEUTIC APPLICATION

The compounds of the invention and their pharmaceutically acceptable salts may be used in human therapy in the form of tablets, capsules, gelatine coated pills, suppositories, ingestible or injectable solutions etc., as regulators of the serotonin-dependent vascular tonus, especially in the treatment of migraines, as anti-thrombosis agents and as thymoanaleptic medicaments with a particularly rapid action (on account of their action on the release of serotonin).

For the foregoing purposes the compounds described above may be administered in a therapeutically effective amount, such as to a mammal; orally or parenterally.

For purposes of injection the compounds described above can be prepared in the form of solutions, suspensions or emulsions in vehicles conventionally employed for this purpose.

The posology depends on the effects required and on the method of administration used. For example, by oral administration, it may be between 15 and 250 mg of active substance per day, with unit doses of between 5 and 50 mg.

Appropriate pharmaceutically acceptable carriers, diluents and adjuvants may be used together with the compounds described herein in order to prepare the desired compositions for use in treatment of mammals according to the invention.

The pharmaceutical compositions of this invention will contain the active compound together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the host.

What is claimed is:

1. A method of treating a mammal afflicted with migraine conditions which comprises administering to said mammal a therapeutically effective amount of a composition containing a compound of the formula:

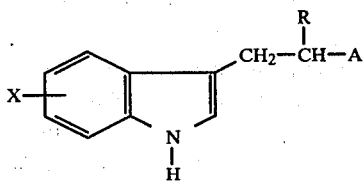

(II)

wherein R represents hydrogen or alkyl having 1 to 3 carbon atoms, X represents hydrogen or halogen and A represents 1,2,5,6-tetrahydro-4-pyridyl, or R represents alkyl having 1 to 3 carbon atoms, X represents hydrogen or halogen and A represents 1,2,3,4,5,6-hexahydro-4-pyridyl, or a pharmaceutically acceptable salt thereof in a pharmaceutically acceptable carrier therefor.

2. The method as claimed in claim 1 which comprises administering 15 to 250 mg of active substance per day or oral administration.

3. A method of treating a mammal to prevent the formation of arterial thrombi which comprises administering to said mammal a therapeutically effective amount of a composition containing a compound of the formula:

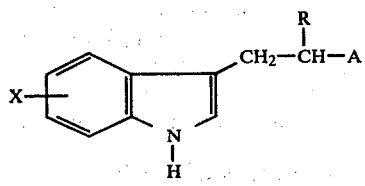

(II)

wherein R represents hydrogen or alkyl having 1 to 3 carbon atoms, X represents hydrogen or halogen and A represents 1,2,5,6-tetrahydro-4-pyridyl, or R represents alkyl having 1 to 3 carbon atoms, X represents hydrogen or halogen and A represents 1,2,3,4,5,6-hexahydro-4-pyridyl, or a pharmaceutically acceptable salt thereof in a pharmaceutically acceptable carrier therefor.

4. The method as claimed in claim 3 which comprises administering 15 to 250 mg of active substance per day by oral administration.

* * * * *